(12) United States Patent
Angeley et al.

(10) Patent No.: US 6,887,233 B2
(45) Date of Patent: May 3, 2005

(54) SCANNING LASER HANDPIECE WITH SHAPED OUTPUT BEAM

(75) Inventors: David G. Angeley, San Jose, CA (US); Dan E. Anderson, Menlo Park, CA (US); Philip S. James, Lafayette, CA (US)

(73) Assignee: Lumenis, Inc., Santa Clara, CA (US)

( * ) Notice: Subject to any disclaimer, the term of this patent is extended or adjusted under 35 U.S.C. 154(b) by 31 days.

(21) Appl. No.: 09/814,443

(22) Filed: Mar. 22, 2001

(65) Prior Publication Data

US 2002/0138119 A1 Sep. 26, 2002

(51) Int. Cl.[7] .............................. A61B 18/18; A61N 1/00
(52) U.S. Cl. ............................... 606/17; 607/88; 606/9; 606/10; 606/11
(58) Field of Search ........................ 606/17, 14, 9–10, 606/11; 219/121.73–121.75; 250/504 H, 504 R; 607/88

(56) References Cited

U.S. PATENT DOCUMENTS

| | | | | |
|---|---|---|---|---|
| 4,534,615 A | * | 8/1985 | Iwasaki ...................... | 385/121 |
| 4,653,495 A | * | 3/1987 | Nanaumi ..................... | 606/16 |
| 4,718,416 A | * | 1/1988 | Nanaumi ........................ | 606/9 |
| 4,807,963 A | * | 2/1989 | Iwasaki ...................... | 385/115 |
| 4,941,734 A | * | 7/1990 | Williams et al. ............ | 359/896 |
| 5,336,217 A | | 8/1994 | Buys et al. | |
| 5,411,502 A | | 5/1995 | Zair | |
| 5,428,699 A | * | 6/1995 | Pon ............................. | 385/31 |
| 5,743,902 A | | 4/1998 | Trost | |
| 6,193,710 B1 | * | 2/2001 | Lemberg ........................ | 606/5 |

FOREIGN PATENT DOCUMENTS

| | | | |
|---|---|---|---|
| JP | 63-137120 | * | 6/1988 |
| JP | 2-252453 | * | 10/1990 |
| WO | 9518984 | * | 7/1995 |

OTHER PUBLICATIONS

Kurt G. Klavuhn, "Illumination Geometry: The Importance of Laser Beam Spatial Characteristics," *Coherent Medical Group Laser Hair Removal Technical Note No. 2*: Feb. 2000, pp. 1–8.

John F. Black et al., "Cooperative Phenomena in Two–Pulse, Two–Color Laser Photocoagulation of Cutaneous Blood Vessels." *Proc SPIE* 4244A–02 May 2001.

John F. Black et al., "Time–domain Optical and Thermal Properties of Blood Undergoing Laser Photocoagulation," *Proc SPIE* 4257A–44 Jul. 2001.

Allen M. Hunter II, et al., "Hair Removal with Nd:YAG Lasers at 1064 nm Wavelength," *ThermoLase Corporation*, Sep. 20, 1996, pp. 1–10, A1, B1.

R. Steiner et al., "The Role of Skin Optics in Diagnostic and Therapeuitc uses of Lasers," *Lasers in Dermatology, Proc of International Symposium, Ulm* Sep. 26, 1989, pp. 1–20.

* cited by examiner

*Primary Examiner*—John A. Jeffery
(74) *Attorney, Agent, or Firm*—Eitan, Pearl, Latzer & Cohen Zadek, LLP

(57) ABSTRACT

A method for delivering electromagnetic radiation onto tissue to be treated with the radiation includes delivering the radiation onto the tissue in a treatment-spot having a polygonal shape such as a rectangle or a hexagon. The polygonal shape is selected such that a region of the tissue to be treated can be completely covered by a plurality of such shapes essentially without overlapping the shapes. The radiation to be delivered is passed through a lightguide having a cross-section of the polygonal shape. Radiation exiting the lightguide is projected onto the tissue via a plurality of optical elements to provide the treatment-spot.

17 Claims, 14 Drawing Sheets

| GROUP | ELEMENT | SURFACE | RADIUS (mm) | THICKNESS (mm) | GLASS |
|---|---|---|---|---|---|
| FIBER 24 | 24B | S0 | | 0.05 | AIR |
| GUIDE 64 | 64A | S1 | | 50.00 | LF5 |
| | 64B | S2 | | 5.30 | AIR |
| GROUP 52 | 70 | S3 | 41.01 | 1.03 | SF10 |
| | | S4 | 4.35 | 3.06 | BAFN10 |
| | 72 | S5 | -6.98 | 5.00 | AIR |
| MIRROR | 60 | S6 | | 6.73 | REFLECT |
| MIRROR | 62 | S7 | | T1 | REFLECT |
| GROUP 54 | 74 | S8 | 30.03 | 4.20 | SSKN8 |
| | | S9 | -24.65 | T2 | AIR |
| | 76 | S10 | -6.50 | 1.80 | SFL6 |
| | | S11 | 15.50 | T3 | AIR |
| | 78 | S12 | 53.57 | 6.00 | BAFN10 |
| | | S13 | -19.84 | T4 | AIR |
| GROUP 56 | 80 | S14 | 34.81 | 11.00 | BAFN10 |
| | | S15 | -22.12 | 2.20 | SF10 |
| | 82 | S16 | -203.48 | 68.00 | AIR |
| TREATMENT | 26 | S17 | | | |

FIG.6A

| SPOT (64M) (mm) | T1 (mm) | T2 (mm) | T3 (mm) | T4 (mm) |
|---|---|---|---|---|
| 6 | 5.27 | 30.33 | 2.73 | 23.81 |
| 4 | 12.61 | 25.48 | 4.00 | 20.05 |
| 2 | 37.58 | 17.77 | 5.79 | 1.00 |

FIG.6B

| GROUP | ELEMENT | SURFACE | RADIUS (mm) | THICKNESS (mm) | GLASS |
|---|---|---|---|---|---|
| FIBER 24 | 24B | S0 | | 0.05 | AIR |
| GUIDE 64 | 64A | S1 | | 50.00 | LF5 |
| | 64B | S2 | | 7.20 | AIR |
| GROUP 52 | 70 | S3 | 41.01 | 1.03 | SF10 |
| | | S4 | 4.35 | 3.06 | BAFN10 |
| | 72 | S5 | −6.98 | 66.0 | AIR |
| GROUP 56 | 80 | S14 | 32.60 | 8.4 | BAFN10 |
| | | S15 | −31.81 | 2.99 | SF10 |
| | 82 | S16 | −799.64 | 75.0 | AIR |
| TREATMENT | 26 | S17 | | | |

FIG.9

| GROUP | ELEMENT | SURFACE | RADIUS (mm) | THICKNESS (mm) | GLASS |
|---|---|---|---|---|---|
| FIBER 24 | 24B | S0 | | 0.05 | AIR |
| GUIDE 64 | 64A | S1 | | 50.00 | LF5 |
| | 64B | S2 | | 7.20 | AIR |
| GROUP 52 | 70 | S3 | 41.01 | 1.03 | SF10 |
| | | S4 | 4.35 | 3.06 | BAFN10 |
| | 72 | S5 | -6.98 | 61.35 | AIR |
| GROUP 56 | 80 | S14 | 32.60 | 8.4 | BAFN10 |
| | | S15 | -31.81 | 2.99 | SF10 |
| | 82 | S16 | -799.64 | 75.0 | AIR |
| TREATMENT | 26 | S17 | | | |

FIG.11

| GROUP | ELEMENT | SURFACE | RADIUS (mm) | THICKNESS (mm) | GLASS |
|---|---|---|---|---|---|
| FIBER 24 | 24B | S0 | | 0.05 | AIR |
| GUIDE 64 | 64A | S1 | | 50.00 | LF5 |
| | 64B | S2 | | 7.20 | AIR |
| GROUP 160 | 162 | S3 | 18.25 | 1.03 | FD10 |
| | | S4 | 3.09 | 3.72 | BAFN10 |
| | | S5 | −5.56 | 6.96 | AIR |
| | 164 | S6 | 5.56 | 3.72 | BAFN10 |
| | | S7 | −3.09 | 1.03 | FD10 |
| | | S8 | −5.56 | 35.60 | AIR |
| GROUP 52 | 70 | S9 | 41.01 | 1.03 | SF10 |
| | | S10 | 4.35 | 3.06 | BAFN10 |
| | 72 | S11 | −6.98 | 61.35 | AIR |
| GROUP 56 | 80 | S12 | 32.60 | 8.4 | BAFN10 |
| | | S13 | −31.81 | 2.99 | SF10 |
| | 82 | S14 | −799.64 | 75.0 | AIR |
| TREATMENT | 26 | S15 | | | |

FIG.13

SCANNING LASER HANDPIECE WITH SHAPED OUTPUT BEAM

TECHNICAL FIELD OF THE INVENTION

The present invention relates in general to devices for delivering laser radiation in laser tissue treatments. The invention relates in particular to a handpiece which shapes a laser beam and scans the shaped beam over tissue to be treated.

DISCUSSION OF BACKGROUND ART

The use of radiation in wavelength-selective, non-ablative laser treatment of dermatological defects is gaining acceptance in the medical community. The term non-ablative here means that the delivery of laser radiation to an area of tissue being treated does not directly cause tissue removal or cause an open wound which must subsequently heal. By way of example, such non-ablative treatments are used, are at least being investigated, for wrinkle (rhytid) reduction, reduction of acne scars, and treatment of vascular disorders such as port-wine stains. Wavelengths most often used in these treatments are in the visible region or the near infrared region of the electromagnetic spectrum.

In these treatments, the area of tissue to be treated is often greater than an area that can be instantly illuminated by a treatment beam. This requires that a treatment beam be moved over the area to be treated until the entire area has received a prescribed dosage of laser radiation. It is important in moving a laser beam over an area to be treated that there are no untreated portions or voids within the treated area. Attempting to avoid such untreated areas by overlapping individual areas corresponding to the instantaneous beam size, however, can lead to a possibility that dosage in overlapped areas can be sufficiently high to cause at least patient discomfort and possibly even wound formation.

One method that may be used to move a beam over an area of tissue to be treated in a controllable manner is to deliver the beam via a hand-holdable scanner (scanning handpiece) which rapidly scans a pulsed beam in a preprogrammed pattern of irradiation spots. One such scanning handpiece is described in U.S. Pat. No. 5,743,902, granted to Trost incorporated herein by reference. This handpiece includes a pair of galvanometer mirrors for performing the programmed scanning. Radiation to be scanned is delivered by an articulated arm to the handpiece. The mirrors in the handpiece direct the radiation to the tissue via a lens for focusing the radiation on the tissue. The mirrors are located at about an effective focal length (EFL) of the lens from the lens, in a telecentric arrangement. This provides that the beam size at the tissue remains about the same with variations in the position of the handpiece from the tissue.

A disadvantage of the Trost handpiece is that it projects an essentially circular beam. This means that individual beam areas must be overlapped to avoid leaving voids in the treatment area. There is also no provision in the handpiece for controlling intensity of radiation over the area of a projected beam. The Trost handpiece is intended primarily for use in ablative applications using mid to long-wavelength infrared radiation. Such applications include skin resurfacing and making surgical incisions. In these applications the overlapping and lack of intensity distribution control present no particular problems.

A scanning handpiece for non-ablative treatments, however, ideally, should project a beam in which the radiation intensity distribution across the beam is as near uniform as possible. Preferably also, the uniform-intensity beam should have a cross-sectional shape such as a square, a rectangle, or a regular hexagon. This would allow an area greater than the beam area to be covered by side-by-side placements (tiling) of beam areas without leaving voids and, if desired, without overlapping. Further, such a scanning handpiece should be configured to receive radiation delivered thereto by an optical fiber. Optical-fiber delivery is a preferred method for delivering visible and near infrared radiation from lasers generating the radiation to a treatment site or a handpiece.

SUMMARY OF THE INVENTION

The present invention is directed to a method for delivering electromagnetic radiation onto tissue to be treated therewith. The invention includes methods and apparatus for forming the delivered radiation into a spot of a particular shape and an inventive method of scanning the delivered radiation over the tissue to be treated.

In a first aspect, the inventive method comprises directing the radiation into a lightguide having a polygonal cross-section of a predetermined shape and projecting an image of an exit-face of the lightguide onto the tissue to be treated such that the radiation is delivered onto the tissue in a treatment-spot having the polygonal shape of the lightguide cross section.

A region of tissue to be treated having an area greater than the area of the treatment-spot is covered by moving the treatment-spot over the treatment region such that the entire region receives the electromagnetic radiation. Preferably the polygonal shape is selected such that a plurality of the shapes can completely fill the area to be treated without overlapping each other.

In a second aspect of the present invention, the lightguide and a plurality of lenses for projecting the lightguide exit-face image form an optical system which can be located in a handpiece arranged to receive the radiation from a source thereof, such as a laser. The radiation is delivered to the handpiece from the source via an optical fiber. In one preferred embodiment of the present invention the optical system includes a scanning arrangement for moving the treatment-spot while the handpiece is held in a fixed relationship to the optical system.

A third aspect of the present invention is directed to an inventive scanning method. In this method the optical elements of the optical system are arranged on an optical axis of the optical system with a first of the elements being arranged to receive the beam of radiation emerging from the lightguide exit-face. The beam of radiation is passed through the optical elements to form the treatment-spot in a treatment plane in which the tissue to be treated is located. Scanning is effected by causing a predetermined relative motion, in a direction transverse to the optical axis, between the lightguide exit-face and at least the first optical element. This causes the treatment-spot to undergo a related transverse motion in the treatment plane.

The relative motion between the lightguide exit-face and the one or more optical elements is related to the treatment-spot motion by the magnification of the combination of the lens elements of optical system. In one example, wherein this magnification is about 6.25, moving the lightguide exit-face by about 1.2 millimeters (mm) causes about 7.5 mm of treatmentspot motion. In another example, wherein the optical elements provide the same magnification, the same treatment-spot motion is achieved by transversely moving two adjacent optical elements, as a group, by only about 0.6 mm with respect to the lightguide.

The relative motion may be effected by moving the lightguide exit-face with respect to the optical elements, or by maintaining the optical fiber in a fixed position and moving one or more of the optical elements with respect to the optical-fiber.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain the principles of the invention.

FIGS. 6A and 6B depict, in tabular form, one preferred prescription for the optical system of FIG. 3.

FIG. 9 depicts, in tabular form, one preferred prescription for the optical system of FIG. 8.

FIG. 11 depicts, in tabular form, one preferred prescription for the optical system of FIG. 10.

FIG. 13 depicts, in tabular form, one preferred prescription for the optical system of FIG. 12.

DETAILED DESCRIPTION OF THE INVENTION

Figure 1:
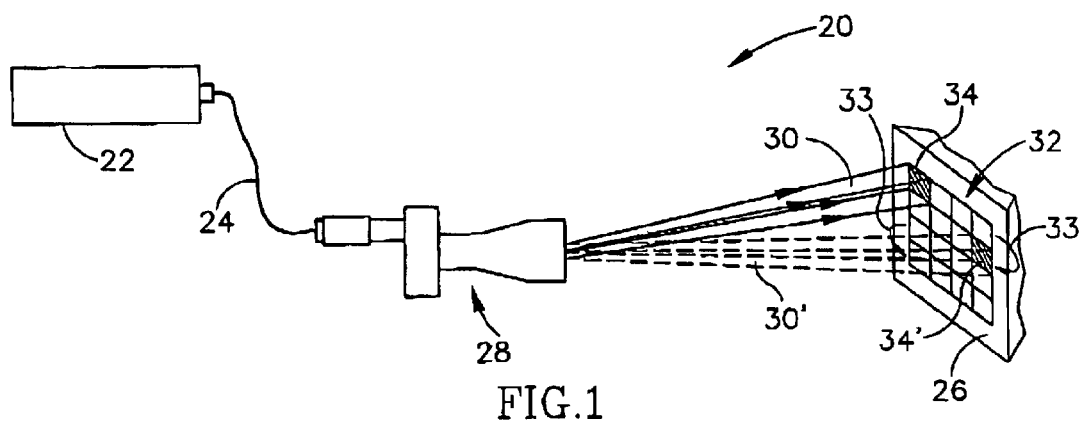
FIG. 1 schematically illustrates a laser treatment apparatus including a laser, an optical fiber receiving and transporting laser-radiation from the laser, and a handpiece in accordance with the present invention including an optical system for receiving laser-radiation from the optical fiber and delivering it to a treatment site.

The type of laser apparatus in which the handpiece of the present invention is to be used is first discussed with reference to FIG. 1 and FIGS. 2A and 2B. Referring first to FIG. 1, laser apparatus 20 includes a laser 22 configured to deliver laser-radiation (electromagnetic radiation) via an optical fiber 24 to treat tissue at a treatment site (treatment-plane) 26.

The optical fiber is connected at its delivery end to the inventive handpiece 28. Transporting the radiation via an optical fiber provides that the laser, or other electromagnetic radiation source can be in a location remote from the location of the treatment-plane. Handpiece 28 provides a convenient means for an operator to steer the laser-radiation 30 delivered by the fiber to a location in the treatment plane. The handpiece includes an arrangement for shaping radiation delivered by optical fiber 24 into a polygonal shape, such as a rectangle or a hexagon, which can be "tiled" to completely cover a treatment area 32 without overlap and without leaving voids or sub-areas which are not irradiated.

Handpiece 28, here, forms radiation into a beam 30 having a square-shaped (rectangular-shaped) cross-section 34 defining the shape of a treatment-spot of the radiation. The terminology without oven , as used above, allows that some minor degree of overlap may be required to allow for the fact that providing a truly "sharp-edged" beam cross-section may not be economically practical. By way of example, a less-than-sharp edge may occupy up to about 15% of the width of a treatment-spot. In such a case, treatment-spots may be overlapped by about 7.5% o minimize the possibility that any area of the tissue is irradiated at a sub-therapeutic level. An area of region of tissue to be treated may also be covered a first time with a "non-overlapping" pattern of treatment-spots, and irradiated one or more additional times using the e or a different pattern.

Still referring to FIG. 1, handpiece 28 includes a scanning arrangement, not shown, which scans the beam over treatment area 32 to cover the area with radiation. This is indicated in FIG. 1 by dotted lines 30' indicating the beam of radiation being projected into another square-shaped sub-area 34' in area 32. The beam can be conveniently scanned in a raster pattern, for example, as indicated by arrows 33. Those skilled in the art will recognize, however, that there are a number of ways in which beam 30 can be scanned across area 32 to "fill" the area with radiation without departing from the spirit and scope of the present invention.

The radiation may be delivered in the form of a sequence of pulses. Each pulse irradiates a particular sub-area of the area to be covered and the scanning mechanism moves the location of pulse incidence on the tissue between successive pulses. Preferably however radiation (CW radiation) is delivered continuously while the beam is being scanned, effectively "painting" the radiation onto the tissue. For example, using a rectangular or square-shaped beam, the radiation can be painted as a series of contiguous "stripes". Radiation dosage per unit area is determined by parameters including output of the laser, the area of the beam, and the scan speed of the beam.

Figure 2A:
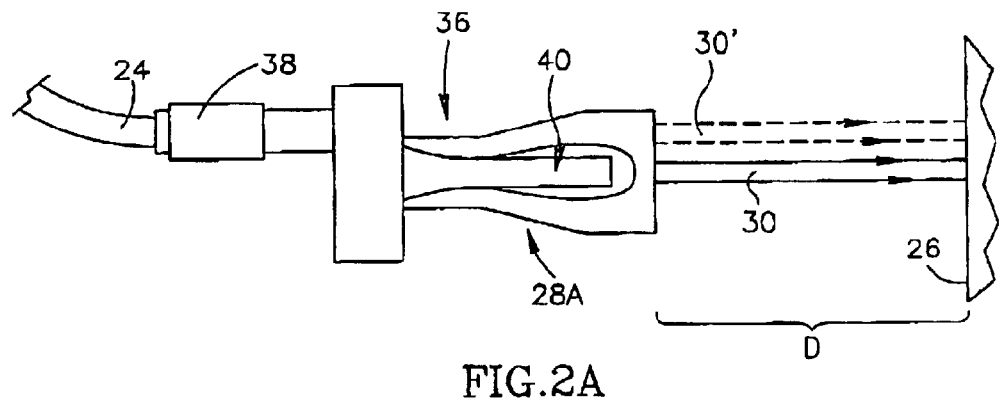
FIGS. 2A–B schematically illustrate various general configurations of handpieces suitable for use in the apparatus of FIG. 1.
Figure 2B:
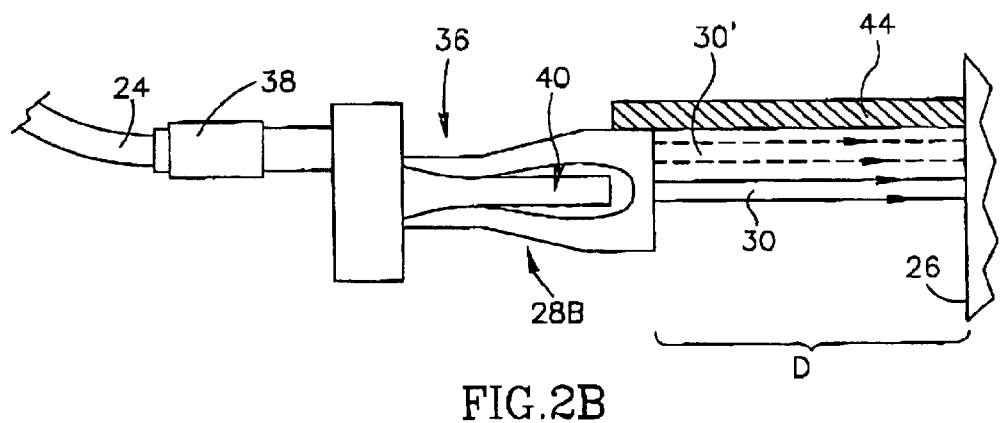

Referring now to FIGS. 2A and 2B, two possible configurations of the inventive handpiece 28 are schematically depicted. An optical system, including a plurality of lenses, a beam scanning arrangement and a beam shaping arrangement is depicted in FIGS. 2A and 2B only in the form of a single unit or "black box" 40. A detailed description of the optical system is presented further hereinbelow. It should be noted that in this description and claims appended hereto, the term "treatment plane" is used in a general sense, recognizing that an area of tissue to be treated, while not being exactly planar, can be considered to be planar within the normal optical tolerances of optical system 40.

Referring first to FIG. 2A, handpiece 28A includes a housing 36 including an optical fiber connector 29 (not shown) for receiving optical fiber 24. In handpiece 28A, positioning of the handpiece at a selected working distance D from treatment plane 26 is left to an operator. In this type of handpiece an "aiming beam" of low power visible radiation is typically delivered along an optical fiber 24 together with treatment radiation 30 (which may or may not be visible). Positioning at the working distance can be judged by the appearance of the aiming beam on the treatment plane, for example, by adjusting the relative position until aiming beam has a minimum width.

In FIG. 2B, a handpiece 28B is equipped with a stand-off probe 44 having a length selected such that, when the probe is placed in contact with treatment plane 26 (tissue to be treated), optical system 40 is a its optimum working distance D. A stand-off arrangement may also take the form of hollow shroud having one end thereof affixed to the handpiece, the free end thereof being placed in contact with the tissue. This is effective in fixing the location of handpiece 28B laterally and longitudinally with respect to the tissue to optimize delivery of radiation in a desired scanning pattern. A stand-off arrangement may also include some device for cooling the skin such a cooled window which is placed in contact with the tissue.

Figure 3:
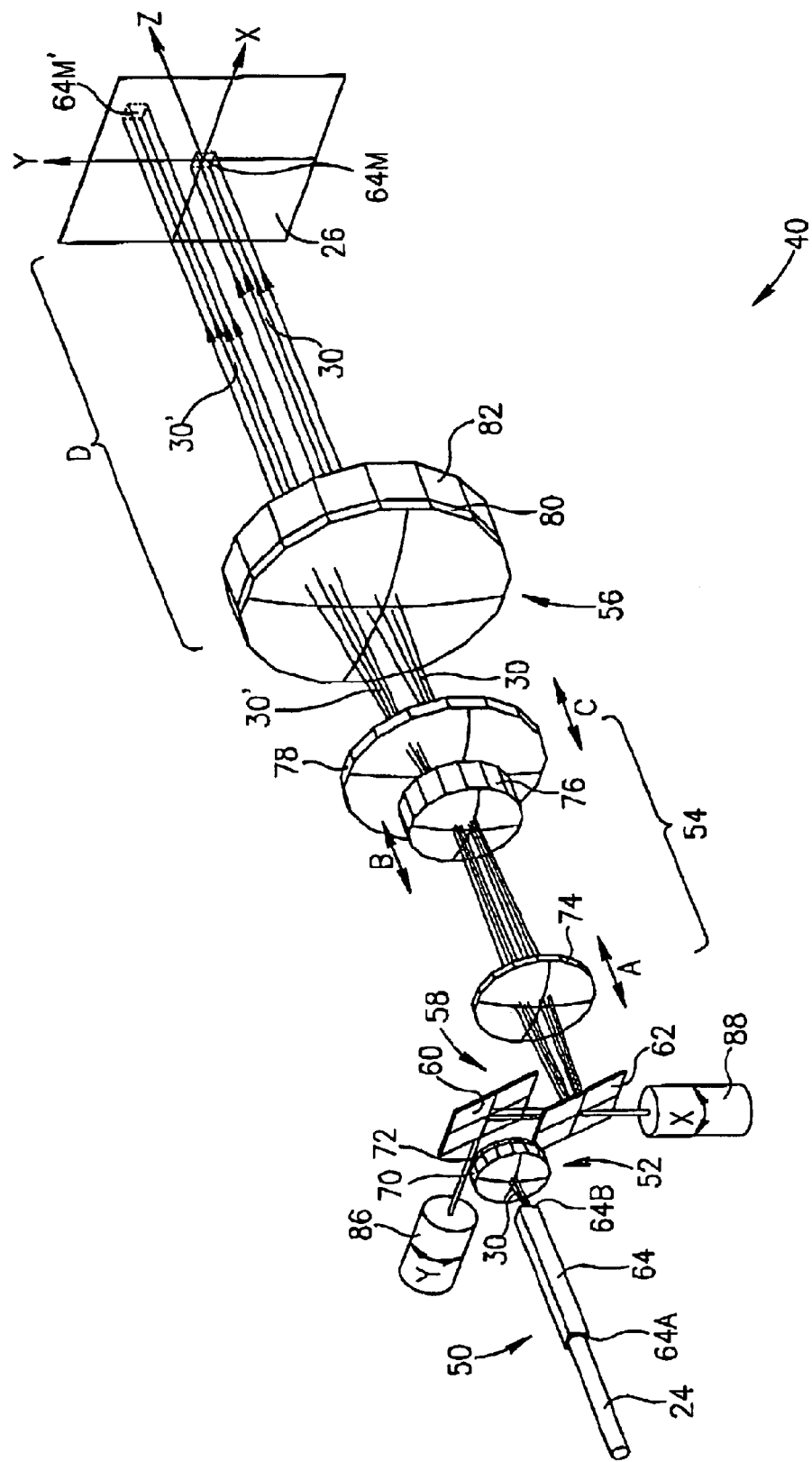
FIG. 3 is a perspective view schematically illustrating one preferred example of the optical system of FIG. 1 including a plurality of lenses arranged to project a radiation spot of selectively variable size, a lightguide for shaping the radiation spot, and galvanometer mirrors for scanning the projected spot over a treatment plane.

Referring now to FIG. 3 a preferred example of optical system 40 is depicted. Optical system 40 includes a beam shaping arrangement 50, lens groups 52, 54, and 56, and a prior-art scanning arrangement 58 comprising two galvanometer mirrors 60 and 62.

Figure 4:
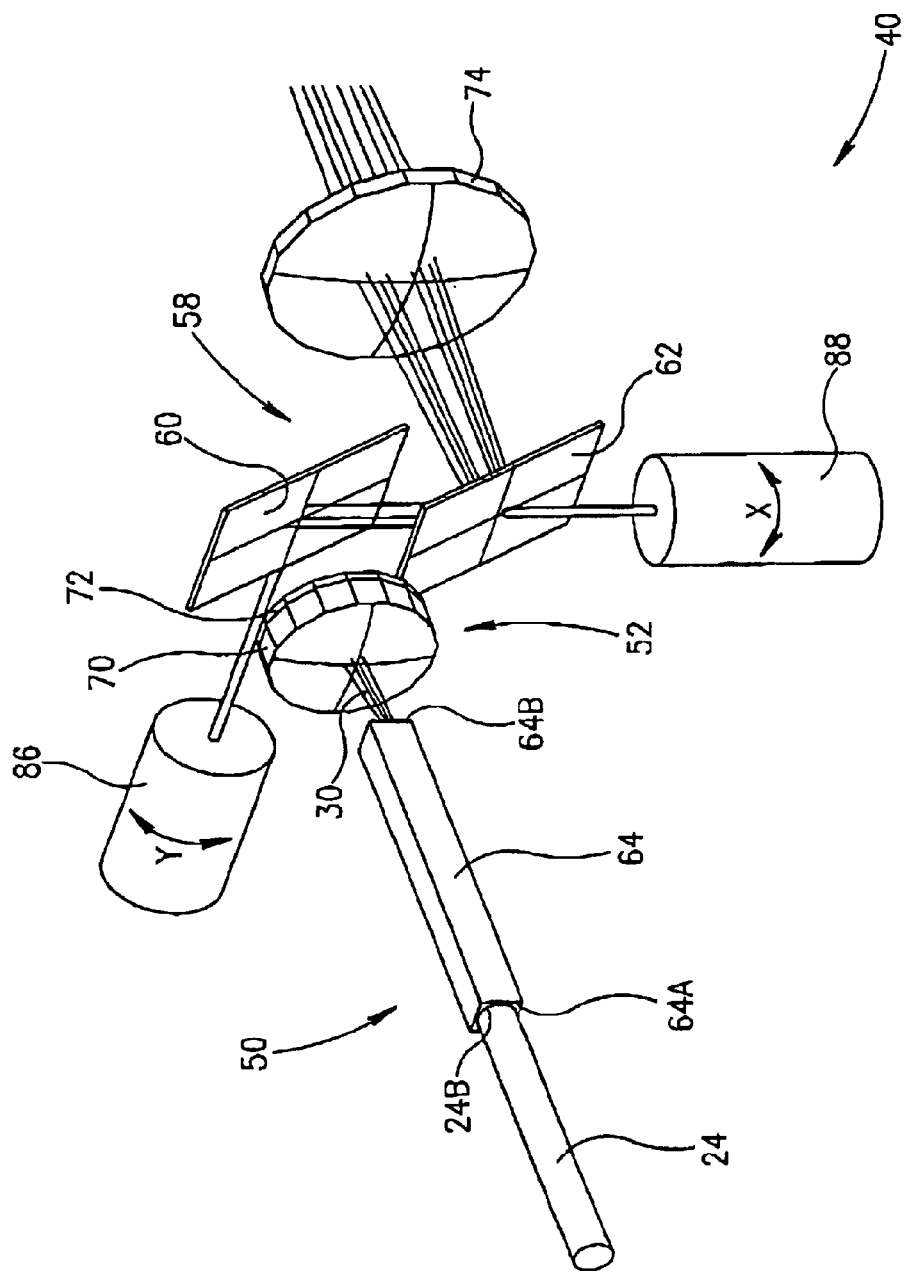
FIG. 4 is a perspective view schematically illustrating details of one preferred example of the beam shaping arrangement of FIG. 3.

Detail of beam shaping arrangement 50 are schematically depicted in FIG. 4. Here, the beam shaping arrangement includes a lightguide 64, preferably made from a length of clad optical fiber having a square core. Lightguide 64 has an entrance face 64A and an exit-face 64B. Lightguide 64 has a cross-sectional shape corresponding to a desired cross-sectional shape of a beam of radiation delivered by optical system 40. Here, lightguide 64 has a square cross-section. As noted above, however, the cross-section can be any polygonal shape that can be "tiled" to cover an area without overlap or void, such as a rectangle or a hexagon. The lightguide is depicted in FIG. 4, for clarity of illustration, as somewhat foreshortened and having a larger cross-section than would be the case in practice.

Lightguide 64 is arranged to receive radiation delivered to handpiece 28 by optical fiber 24, here also having an exaggerated cross-section. Lightguide 64 preferably has a larger cross section-area and a larger numerical aperture (NA) than those of optical fiber 24. Handpiece 28 and fiber connector 29 (not shown) thereof are preferably arranged such that optical fiber 24 butt couples to lightguide 64. It is also possible to provide a lens arrangement for coupling radiation from optic fiber 24 into lightguide 64. This could, however, add inconveniently to the length of handpiece 28.

In a butt-coupled arrangement, the cross-section area and NA of the lightguide 64 are preferably selected such that all radiation leaving optical fiber 24 enters entrance face 64A of optical fiber 64, except that radiation which is lost by Fresnel reflection at the entrance face. This reflection loss, of course, can be reduced by providing a suitable antireflection coating on entrance face 64A. A preferred diameter for optical fiber 24 is 0.365 millimeters (mm) and a preferred cross-section dimension (here, the side of a square) for lightguide 64 is about 0.4 mm. Optical fiber 24 preferably has an NA of about 0.22 and lightguide 64 preferably has an NA of 0.24.

This arrangement of optical fiber and lightguide provides that each transmission mode of radiation exiting optical fiber 24 can propagate along lightguide 64 in two or more different modes. One effect of this is to smooth-out the intensity distribution of radiation at exit-face 64B of the lightguide.

This intensity-smoothing is advantageous in itself, as it minimizes the possibility that there can be points in the beam where intensity may inadvertently exceed an ablation-threshold value or inadvertently fall below a therapeutic value. The intensity-smoothing is also effective in uniformly filling the exit-face of lightguide 64 such that at this exit-face the radiation has a well-defined cross-sectional shape corresponding to the cross-sectional shape of the lightguide.

It has been determined that launching radiation into lightguide 64 from a multimode optical fiber increases the effectiveness of the lightguide in intensity-smoothing and shaping laser radiation at exit-face 64 compared with that which would be experienced were radiation focused into the lightguide directly from a laser. The polygonal cross-section of the light provides that equivalent intensity-smoothing is accomplished in a significantly shorter distance than would be the case were the lightguide circular in cross-section. It has been determined that because of this increased effectiveness, smoothing and shaping of the radiation can be accomplished by a lightguide having a length of 50.0 millimeters (mm) or less and even as short as 25 mm or less. This allows the light guide to be incorporated into handpiece 28 without adding inconveniently to the length of the handpiece. The degree of beam uniformity obtained will depend, inter alia, on the length of lightguide 64 and its cross-sectional shape. In most treatments an intensity variation of less than about ±20% of a nominal value can be considered about uniform.

Using a lightguide such as lightguide 64 to shape a projected beam offers considerable advantages over using a shaped physical aperture-stop, i.e., an opaque member having a shaped aperture therein. By way of example, such an aperture stop usually functions by "trimming" edge portions of an essentially round beam to form the shaped beam. The trimmed portions of the beam represent energy lost from the beam so beam delivery becomes correspondingly inefficient. Further, the stop itself can be heated or even damaged by the radiation that is stopped thereby. Providing a means of removing heat from a handpiece would add considerably to the complexity and cost of the handpiece. Laser damage to the stop, or course, would also limit the useful life of a handpiece.

Continuing now with reference again to FIG. 3, optical system 40 includes lens groups 52, 54, and 56, and a scanning arrangement 58 comprising two galvanometer mirrors 60 and 62. The lens groups are arranged as a telecentric "zoom" or variable-magnification optical system. Lens group 52, here, is a cemented doublet lens having positive power and comprising lens-elements 70 and 72.

Exit-face 64B of lightguide 64 is located at about a focal length of lens group 52 from the lens group 52 and approximately collimates radiation received from lightguide 64. The approximately-collimated beam is directed by galvanometer mirrors 60 and 62 to lens group 54. Lens group 54, here, includes a lens 74 having positive dioptric power, a lens 76 having negative dioptric power, and a lens 78 having positive dioptric power. The group of lenses is arranged as an approximately afocal lens group of variable magnification. Magnification is altered by selectively moving the lenses with respect to each other and with respect to lens groups 52 and 56 as indicated by arrows A, B, and C.

The beam exiting group 54 is incident on lens group 56, here a cemented doublet lens having positive power, and comprising lens-elements 80 and 82. Lens group 56 is arranged to focus the beam incident thereon, thereby providing a magnified image 64M of lightguide exit-face 64B in plane 26 at working distance D from optical system 40. The lateral position of the magnified image is determined by the orientation of the galvanometer mirrors 60 and 62 which are adjusted by motors 86 and 88 respectively. Mirrors 60 and 62, as indicated by arrows Y and X on motors 86 and 88, adjust respectively the Y and X locations of an image in plane 26. This is illustrated by beam 30' forming a magnified image 64M' in plane 26. Here, it should be noted that the magnified images 64M and 64M' correspond to sub-areas 34 and 34' of FIG. 1 and are referred to alternatively hereinafter as a treatment-spot.

It is important in optical system 40 that lens groups 54 and 56 be arranged such that galvanometer mirrors 60 and 62 be axially located at about an EFL (effective focal length) from lens groups 54 and 56 (considered together as a sub-system) at all magnifications. Those skilled in the art will recognize that the EFL is determined from a principal plane (not shown) of the sub-system and the location of this plane will vary as lenses thereof are moved to change the magnification. The mirrors are also located at an EFL of lens group 52 from lens group 52. This relationship of the mirrors to the lenses maintains the telecentricity of the system. This telecentricity provides minimal variation of the beam shape and scan pattern as a function of working distance.

It is also important that scanning arrangement 58 be arranged in optical system 40 such that the beam is steered thereby before it passes through lens group 54. This ensures that the beam size and location on mirrors 60 and 62 is about the same at all magnifications. This provides that the size of the mirrors can be minimized, which in turn provides for rapid response and scanning speed of the galvanometer arrangement.

Figure 5:
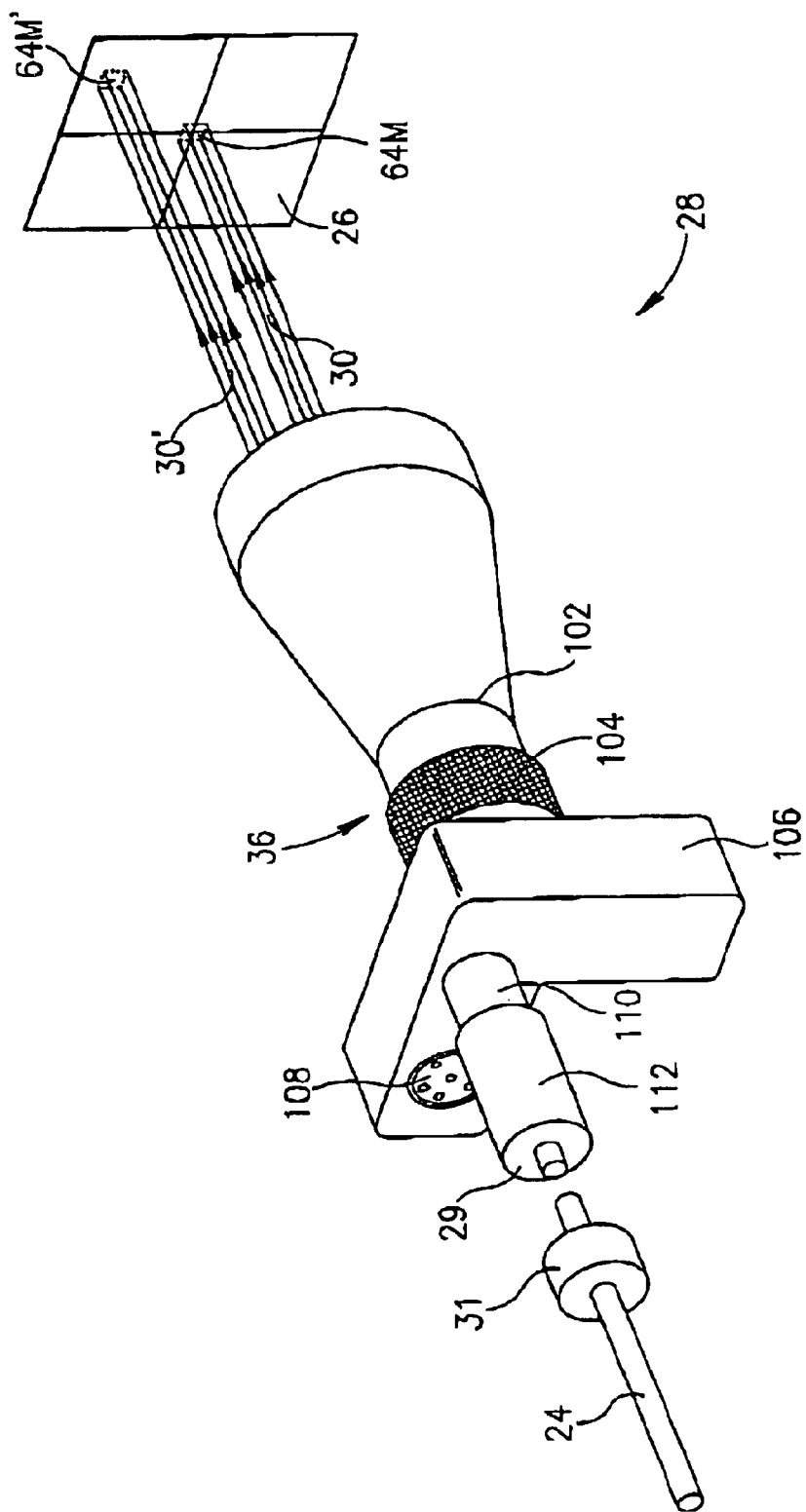
FIG. 5 schematically illustrates a preferred configuration of a housing for a handpiece incorporating the optical system of FIG. 3.

Continuing with reference to FIG. 3, and additionally to FIG. 5, details of a housing 36 for handpiece 28 incorporating above-described optical system 40 are illustrated. Housing 36 includes a forward portion 102 arranged to accommodate lens groups 54 and 56 of optical system 40. A rotatable collar 104 is provided for driving pin and slot cam arrangements that cooperatively move lenses 74, 76, and 78 of lens group 54 for selectively varying the size of a projected treatment-spot 64M. As such lens-moving mechanisms are well known in the optical art, such a mechanism is not depicted or described in detail herein.

Housing 36 includes a central portion 106 configured to accommodate galvanometer mirrors 60 and 62 and motors 86 and 88 for driving the mirrors. Central portion 106 of housing 36 includes an electrical connector 108 to facilitate providing power and electronic scanning instructions to motors 86 and 88 therein.

Attached to central portion 106 of housing 36 is an intermediate portion 110 configured to hold lens group 52 of optical system 40. Attached to intermediate portion 110 is an input portion 112 configured to hold beam-shaping lightguide 64. Input portion 112 includes fiber connector 29 configured to mate with a corresponding connector 31 on optical fiber 24. Connectors 29 and 31 are cooperatively arranged to maintain a desired spatial relationship between optical fiber 24 and entrance face 64A of lightguide 64.

Preferably, input portion 112 is removeably attached to housing 36. This allows the input portion to be detached and replaced with an input portion including a lightguide 64 having a different cross-section for providing a different projected treatment-spot shape.

A preferred prescription for an optical system 40 is depicted in tabular form in FIGS. 6A and 6B. This prescription assumes that optical fiber 24 and lightguide 64 have numerical apertures of 0.22 and 0.24 respectively. Optical fiber 24 is assumed to have a (core) diameter of 0.365 mm, and lightguide 64 is assumed to have a 0.4 mm square (core) cross-section. Each optical element is identified by reference numeral in FIGS. 6A and B, is additionally characterized by a surface number, as is treatment plane 26. Surfaces are numbered consecutively S0 through S17 in the direction in which radiation progresses through the optical system. This prescription form will be familiar to those familiar with the optical design art.

In FIG. 6A variable lens separations for moveable lenses (optical elements) 74, 76, and 78 are designated, T1, T2, T3, and T4 respectively. Values of these separations for different sizes of spot 64M are depicted in FIG. 6B.

Figure 7:
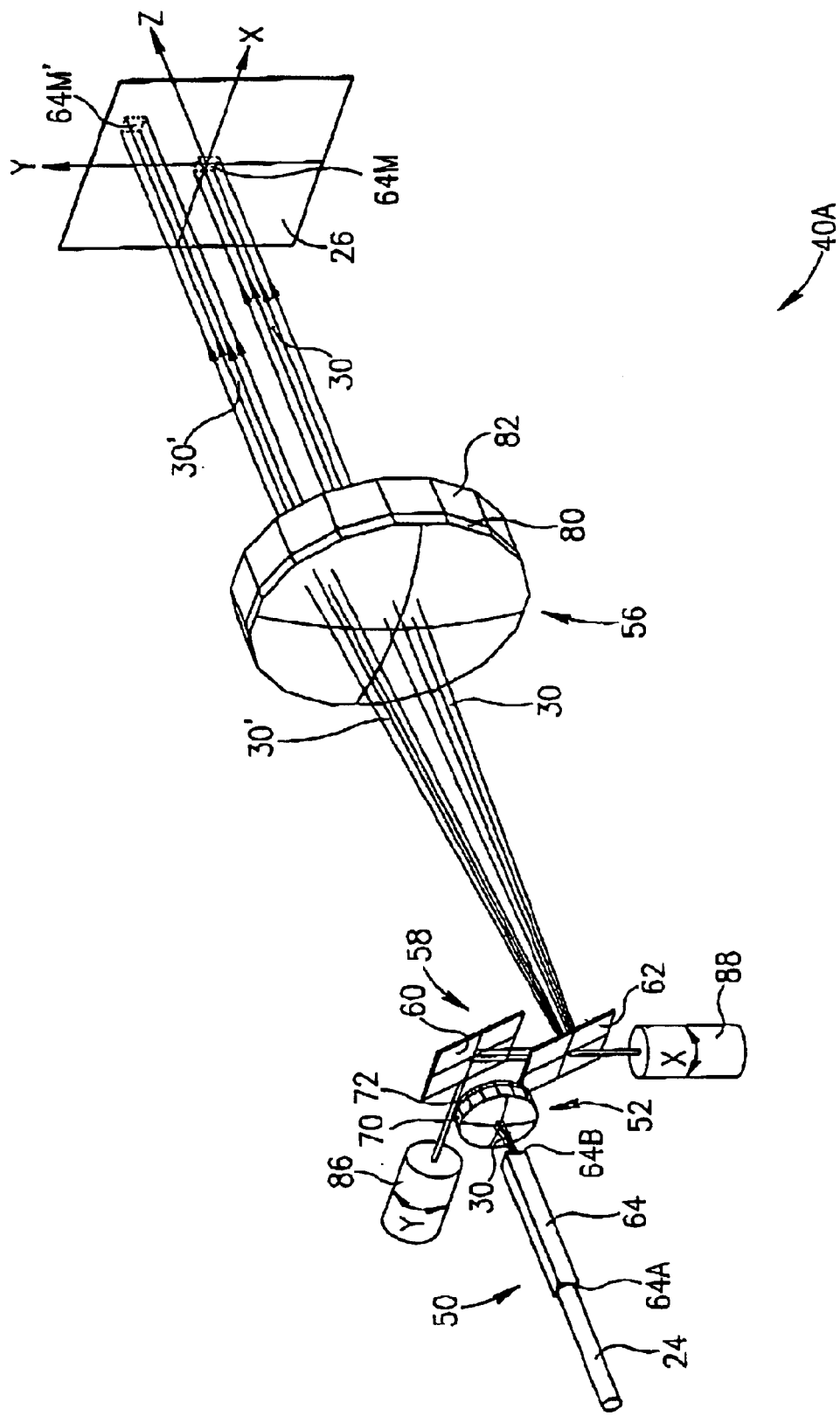
FIG. 7 is a perspective view schematically illustrating another preferred example of the optical system of FIG. 1, similar to the optical system of FIG. 3 but wherein the lenses are arranged to project a radiation spot of fixed size.

Referring now to FIG. 7, another embodiment 40A of an optical system suitable for a handpiece 28 in accordance with the present invention is illustrated. Optical system 40A is a fixed-magnification optical system and, accordingly, simpler in its arrangement than optical system 40 of FIG. 3. Optical system 40A is similar to optical system 40, with an exception that it does not include the variable-magnification lens-group 54 thereof.

In optical system 40A, lens groups 52 and 56 are spaced apart by a distance equal to about the sum of the focal lengths of the lens groups. Galvanometer mirrors 60 and 62 are preferably located at about one EFL of lens group 52 from lens group 52 and about one focal length of lens group 56 from lens group 56.

In embodiments of the inventive handpiece described above, beam scanning is accomplished by a pair of galvanometer mirrors (mirrors 60 and 62). Such a galvanometer mirror scanning arrangement is reliable, fast, and can provide a wide scanning range. However, as can be seen from FIG. 5, incorporation of such a scanning arrangement in a handpiece requires that the handpiece housing include a relatively bulky appendage (portion 106 of housing 36) for housing mirrors and associated driving motors of the arrangement. This appendage can detract somewhat from the convenience of use of a handpiece.

Figure 8:
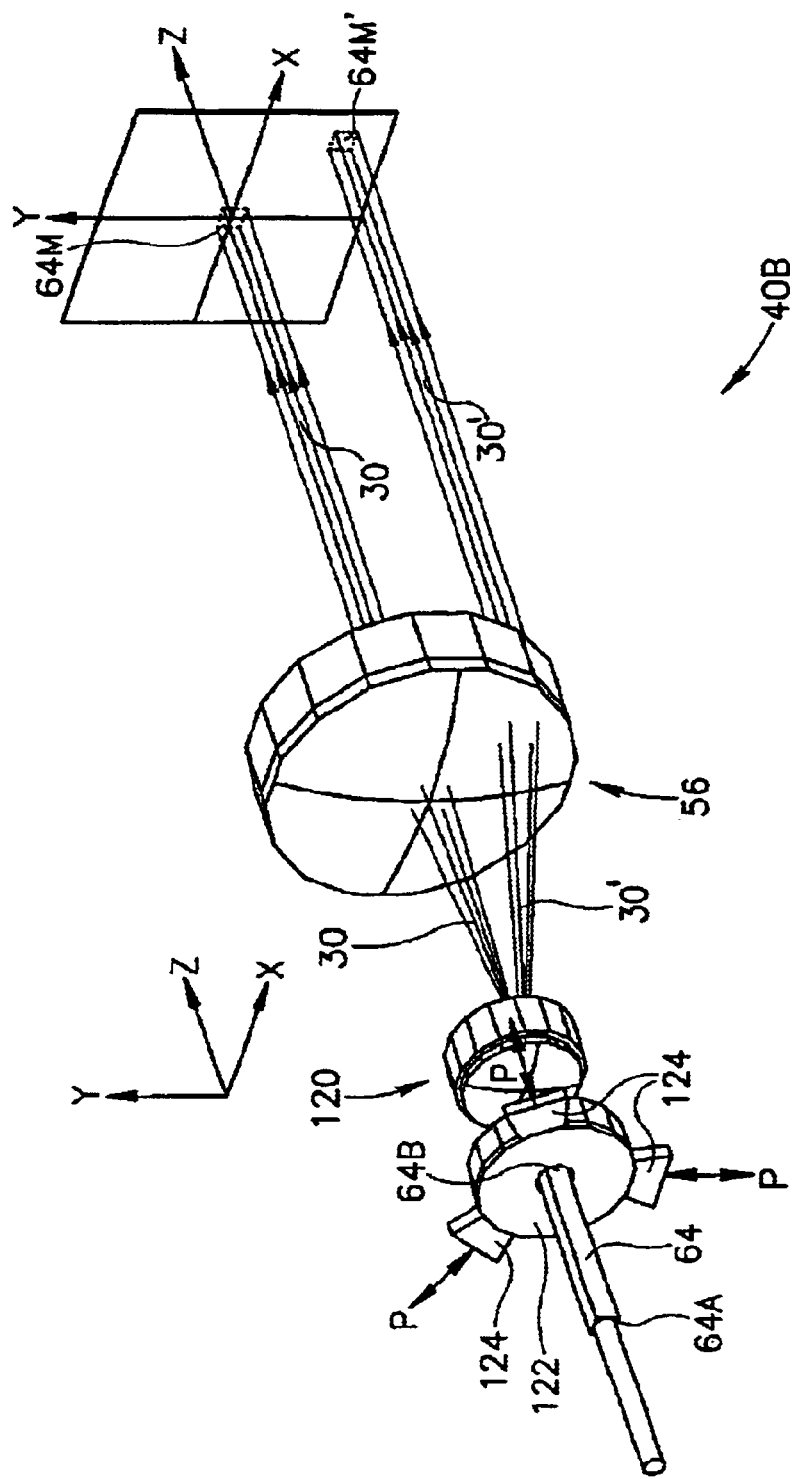
FIG. 8 is a perspective view schematically illustrating yet another preferred example of the optical system of FIG. 1, including a plurality of lenses arranged to project a radiation spot of fixed size, a lightguide for shaping the radiation spot and wherein the projected spot is scanned over the treatment plane by correspondingly moving the lightguide.

Referring now to FIG. 8, an optical system 40B in accordance with the present invention has a fixed magnification arrangement including lens groups 52 and 56 arranged generally as described above for optical system 40A but without galvanometer mirrors therebetween. In optical system 40B, treatment-spot scanning is accomplished by an inventive scanning arrangement 120 cooperative with beam-shaping lightguide 64. In this arrangement, exit-end 64B of lightguide 64 is held in a mount 122 which is moveable by piezo-electric actuators 124 as indicated by arrows P. By applying suitable potentials and frequencies to the actuators the end of lightguide 64 can be moved in an X-Y plane (see XYZ coordinate diagram in FIG. 8) perpendicular to the general propagation (axial) direction Z of radiation through the optical system. Those skilled in the art will recognize that lens groups of this and other optical system designed are arranged on an optical axis (not shown) being parallel to the Z direction.

Optical system 40 is arranged to form a magnified image of exit-face 64B of lightguide 64 in treatment plane 26. Accordingly, as the exit-face is moved, the image 64M of the exit-face (the treatment-spot) moves (also in an X-Y plane transverse to axial direction Z) by an amount about equal to the distance moved by the exit-face multiplied by the linear magnification of optical system 40B, as indicated by spot 64M'.

It should be noted here that piezo-electric scanning arrangement 120 is only schematically depicted in FIG. 8 for simplicity of illustration. In practice such an arrangement may be significantly more complex and may include a different number and different action of piezo-electric actuators. One suitable device for providing the desired scanning motion is a Model P105 optical-fiber positioner available from Micro Pulse Systems, Inc., of Santa Barbara, Calif. This device includes three pairs of piezo-electric actuators which translate linear motion of the actuators to lateral motion of a mount by contact with three wedge-shaped ridges arranged to form a kinematic bearing. Lateral motion of up to 1.5 mm from a nominal center position is possible. It should also be noted here that scanning arrangement 120 may be driven by means other than piezo-electric means without departing from the spirit and scope of the present invention. By way of example, electromagnetic actuation may be used.

Still referring to FIG. 8, it is important that as the exit-end of lightguide 64 is moved, exit-face 64B thereof remains at least axially aligned in the X-Y plane with optical fiber 24. If light guide 64 has a sufficiently great length-to-cross-section ratio, end 64A thereof can be rigidly and fixedly held while the motion of end 64B thereof is accommodated by flexure of the lightguide itself. This arrangement has an advantage that the exit-face of optical fiber 24 and lightguide entrance-face 64A are maintained parallel to each other as lightguide exit-face 64B is moved. A long lightguide, however, may add inconveniently to the length of the inventive handpiece.

Alternatively, end 64A of lightguide 64 may be held in a non-rigid bearing which permits some degree of rotary motion about the X and Y axes. Such a bearing, for example may be formed by maintaining lightguide-end 64A in an aperture in a rigid mount (not shown in FIG. 8) with the lightguide-end surrounded and maintained in the aperture by an elastomeric bushing. This will result in a change in angular alignment of the adjacent faces of lightguide 64 and optical fiber 20. This change of alignment, however, can be kept sufficiently small that lightguide 64 can still collect essentially all radiation delivered by optical fiber 24 over a useful range of motion of lightguide exit-face 64B. By way of example, displacing one end of a 50.0 mm long lightguide by 1.0 mm will cause only about 20 milliradians (mr) of angular misalignment. This is equivalent to only about 0.02 of NA which can be easily accommodated by providing that lightguide 64 has at least a correspondingly greater NA than that of optical fiber 24. This misalignment may be reduced if some of the lateral motion of the lightguide is accommodated by flexure thereof. One preferred specification for the optical system of FIG. 8 is depicted in tabular form in FIG. 9.

In this system, a lateral motion for spot 64M of 7.5 mm is possible with a 1.2 mm motion of lightguide exit-face 64B. Using a lightguide 64 having a 0.4 mm square cross-section of on the side, spot 64M will have a 2.5 mm square form. This represents a magnification of about 6.25.

Figure 10:
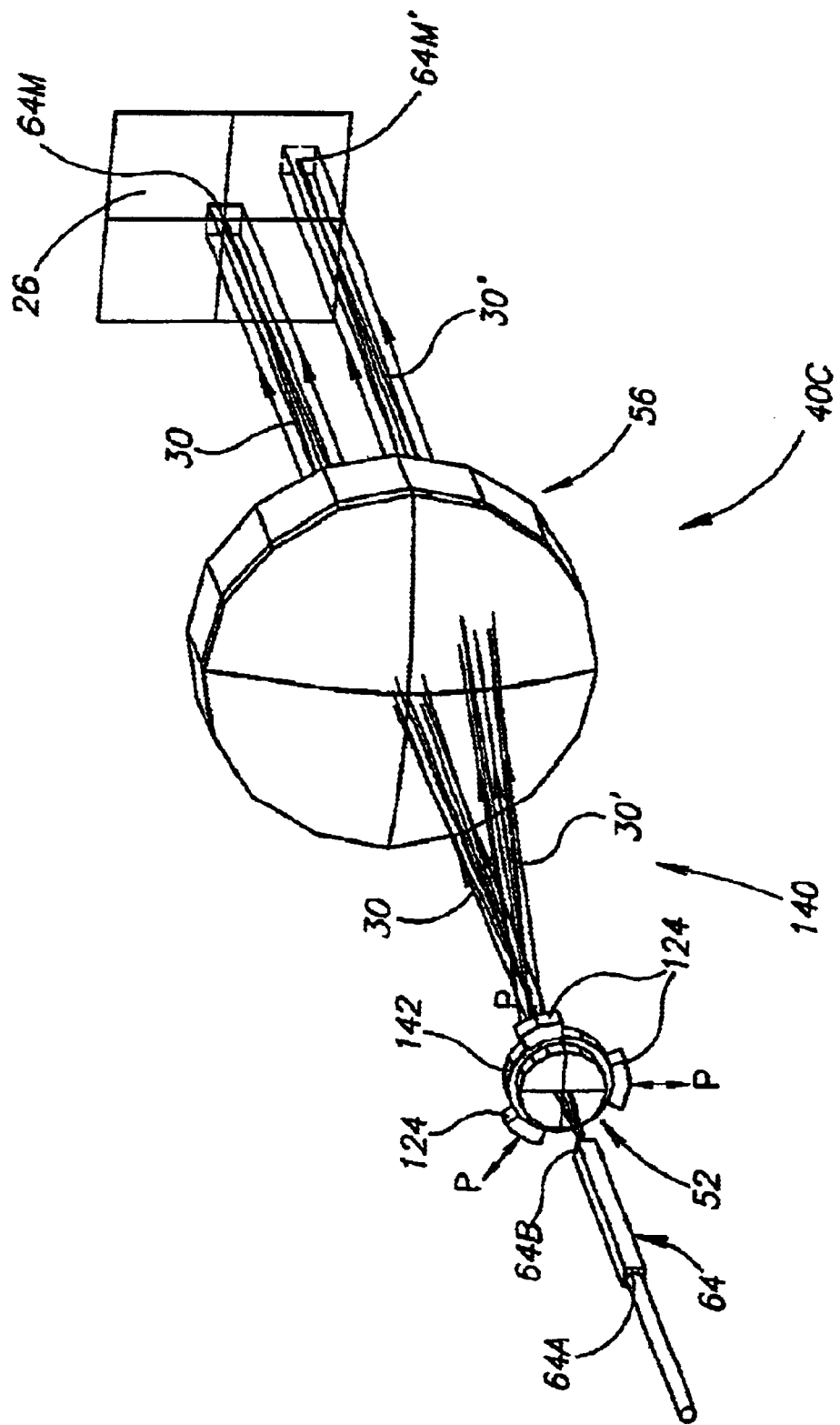
FIG. 10 is a perspective view schematically illustrating still another preferred example of the optical system of FIG. 1, including a plurality of lenses arranged to project a radiation spot of fixed size, a lightguide for shaping the radiation spot, and wherein the projected spot is scanned over the treatment plane by correspondingly moving a particular one of the lenses with respect to the lightguide.

Referring now to FIG. 10 an optical system 40C in accordance with the present invention has a fixed magnification arrangement including lens groups 52 and 56 arranged generally as described above for optical system 40B. In optical system 40C, treatment-spot scanning is accomplished by an arrangement 140, again, cooperative with beam-shaping lightguide 64. In this arrangement, however, lightguide 64 is held in axial and angular alignment with optical fiber 24 as in optical systems 40 and 40A. Lens group 52 is held in a mount 142 driven by piezo-electric actuators as indicated by arrows P. Treatment-spot scanning is accomplished by moving lens group 52, as indicated by arrows P, relative to lightguide exit-face 64 in an X-Y plane. One preferred specification for the optical system of FIG. 10 is depicted in tabular form in FIG. 11. In this system, the relationship between the amount of relative motion between lightguide 64 and lens group 52 and the corresponding motion of treatment-spot 64M is the same (for the same magnification of optical systems 40B and 40C) as in optical system 40B.

Figure 12:
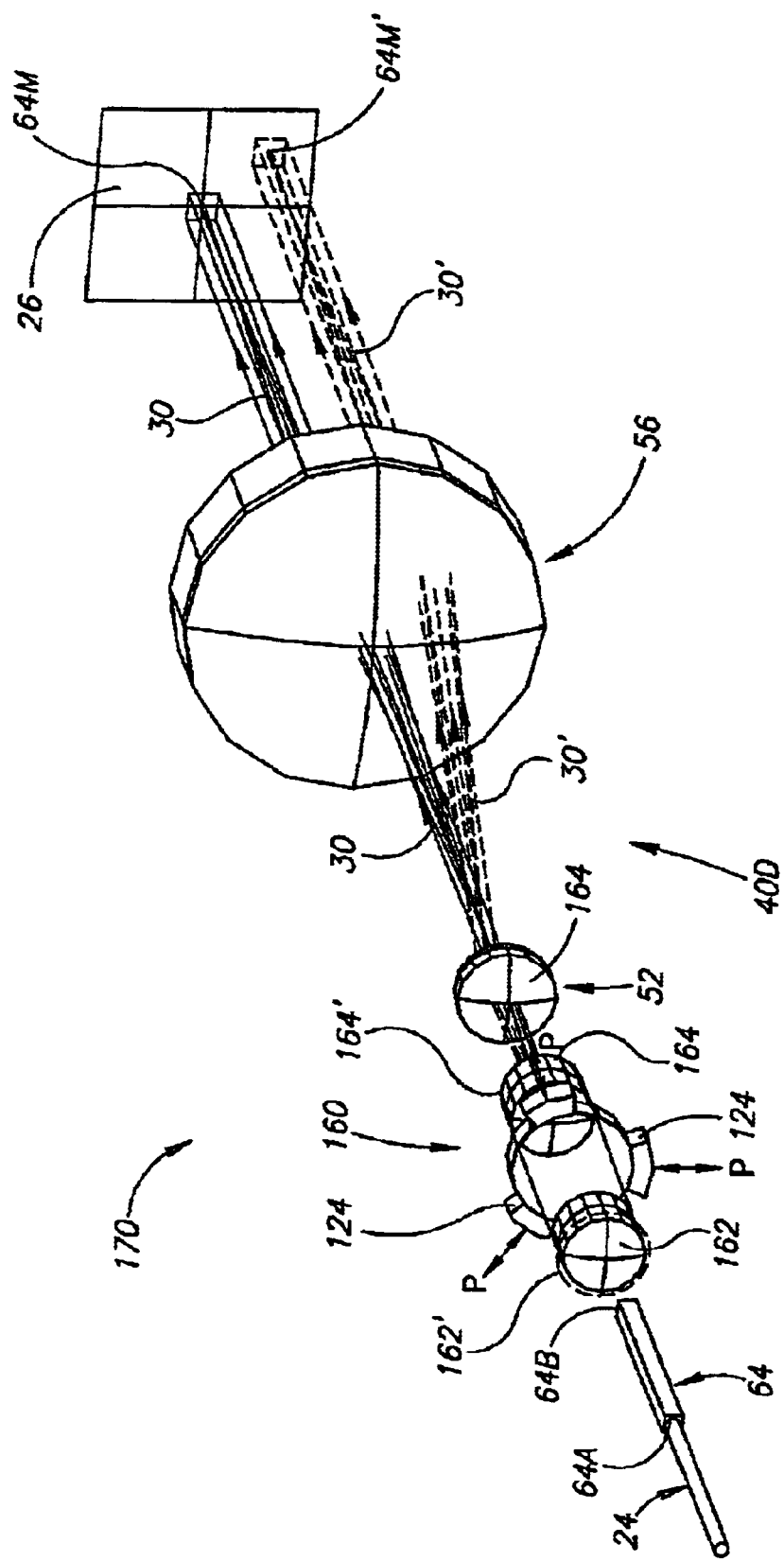
FIG. 12 is a perspective view schematically illustrating a further preferred example of the optical system of FIG. 1, including a plurality of lenses arranged to project a radiation spot of fixed size, a lightguide for shaping the radiation spot, and wherein the projected spot is scanned over the treatment plane by correspondingly moving a relay-group of the lenses with respect to the lightguide.

Referring now to FIG. 12, an optical system 40D in accordance with the present invention has a fixed-magnification arrangement including lens groups 52 and 56 arranged generally as described above for optical system 40B. Additionally, optical system 40D includes a unit magnification (telecentric) relay lens group 160, including doublet lenses 162 and 164.

In optical system 40D, treatment-spot scanning is accomplished by an arrangement 170 cooperative with beam-shaping lightguide 64. In this scanning arrangement, lightguide 64 is held in alignment with optical fiber 24, as in optical system 40C, and lens group 160 is moved as a unit. This is indicated by arrows P and by broken lines 162' and 164' representing respectively lenses 162 and 164 in a transversely displaced position. One preferred specification for the optical system of FIG. 12 is depicted in tabular form in FIG. 13.

An advantage of optical system 40D and scanning arrangement 170 associated therewith is that motion of relay-lens group 160 moves treatment-spot 64M by an amount equal to twice the magnification of the optical system multiplied by the relay lens motion. Accordingly, for an optical sub-system comprising lens groups 52 and 56 having a magnification of about 6.2, a 7.5 mm treatment-spot motion can be effected by moving relay lens group 160 by only about 0.6 mm. This has an advantage in reducing demands on a piezoelectric arrangement or the like for moving the relay lens group, albeit at the expense of increasing the length of the inventive handpiece to accommodate the relay-group 160.

It should be noted here that the movement multiplying factor provided by relay 160 would be different were the magnification of the relay other than unity. While unit magnification for relay 160 is preferred, the relay may have any other magnification, greater or less than unity without departing from the spirit and scope of the present invention.

Figure 14:
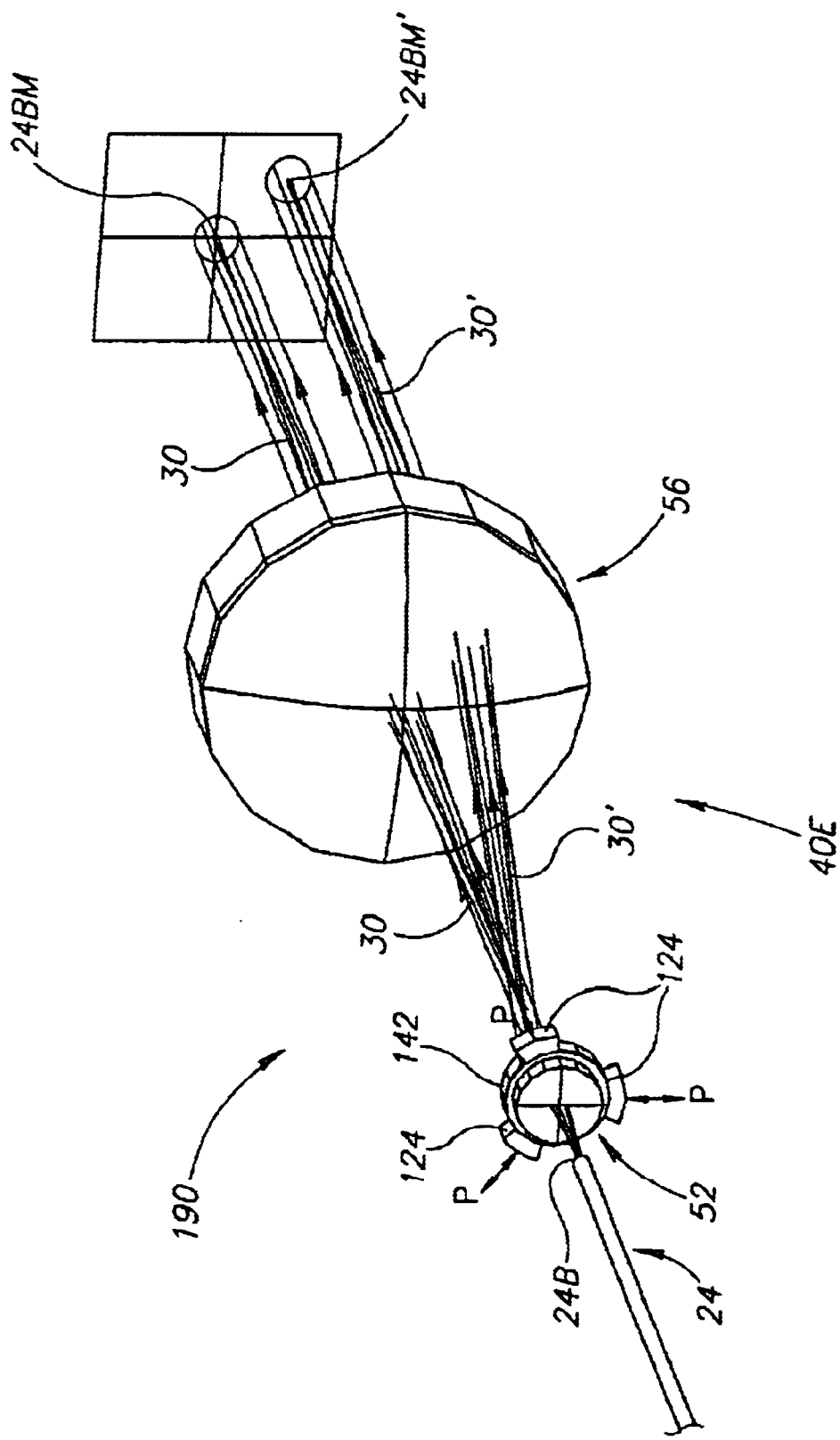
FIG. 14 is a perspective view schematically illustrating a still yet another preferred example of the optical system of FIG. 1, similar to the optical system of FIG. 10 but wherein the lightguide is omitted and is substituted by a circular cross-section fiber delivering radiation from a source thereof to the optical system.

Those skilled in the art will recognize that the inventive scanning principle of optical systems 40B–D is useful in a handpiece even without the inclusion of a separate lightguide for beam shaping. By way of example, FIG. 14 depicts an optical system 40E, similar to optical system 40C but absent beam-shaping (treatment-spot shaping) lightguide 64 omitted. In optical system 190, optical fiber 24 delivering the radiation from laser 22 (see FIG. 1) to the optical system is held with exit-face 24B thereof at about one focal-length of lens group 52 from the lens group. Those skilled in the art will recognize that optical fiber 24 may also be described as a lightguide. Exit-face 24B is imaged by lens groups 52 and 56 to form the treatment-spot, here designated 24M and 24M'.

The treatment-spot in this case will have whatever shape optical fiber 24 has. In FIG. 14, this cross-section, for consistency of description is depicted as circular, providing correspondingly shaped treatment-spots 24BM and 24BM'. Clearly, optical fiber 24 could have a polygonal cross-section for providing a polygonal spot. The arrangement of optical system 40E, having no provision for smoothing intensity distribution of radiation delivered by fiber 24, can be expected to provide treatment-spots having somewhat less uniform distribution of intensity than optical systems 40 and 40A–40D.

It should be noted here that while the scanning arrangements of optical systems 40B–D have each been described in the context of a relatively-simple, fixed-magnification optical system, the scanning arrangements are also useable in a variable-magnification optical system such as optical system 40. Indeed, in a variable magnification system, eliminating the need for intra-optical system galvanometer mirrors has an advantage in addition to simply eliminating a somewhat inconvenient appendage from the housing of the inventive handpiece. This advantage is that a greater range of lens motion is possible for moveable elements of the lens because of the elimination of the galvanometer mirrors. The greater range of movement can be used to simplify the design of the optical system, for example, to provide a greater range of magnification, more precise correction of aberrations, or effectiveness over a wide range of different radiation wavelengths.

While beam-shaping and scanning aspects of the inventive handpiece are described above with reference to one fixed-magnification and one variable-magnification optical system, these optical systems should not be considered as limiting the invention. Those skilled in the optical design art, from the description provided herein, may devise other optical systems that are usable with the inventive beam-shaping and scanning arrangements. Such systems may include more optical elements than are included in systems described above, or the same number of elements, or less elements with one or more thereof having a gradient refractive index or an aspheric surface.

Figure 15:
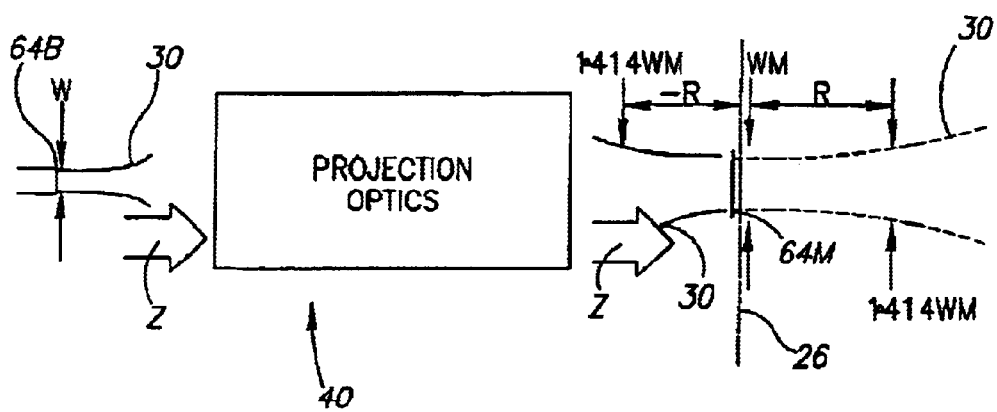
FIG. 15 schematically illustrates a preferred imaging scheme in an optical system of a handpiece in accordance with the present invention.

Whatever optical system is selected, it is preferable that projection optics thereof are designed according to a principle depicted schematically in FIG. 15. The principle involves projecting onto treatment plane 26 a magnified image 64M of exit-face 64B of lightguide 64 with the beam 30 (correspondingly magnified and having the same uniformity of distribution) emerging from it. The projection of the emerging beam is depicted, here, in phantom to indicate that, in practice it would be absorb in tissue in plane 26. The projection direction is indicated by arrows Z.

As far as forming a magnified image of the lightguide exit-face is concerned, this can be approached in the manner of forming an image (in an image plane) of any remotely illuminated two-dimensional object. The two-dimensional object, here, is lightguide exit-face 64B. Forming this image defines the shape of the treatment-spot 64M. Were this imaging the only design concern, an optical system could be designed entirely using standard geometric ray tracing techniques. The radiation used for the treatment, however, is not radiation from a remote illuminating source reflected from the end face of the optical fiber, but is the laser-radiation beam emerging from lightguide 64.

The emerging beam can be considered as having a narrowest point or waist W at lightguide exit-face 64B. The beam has particular characteristics imposed by the lightguide, and propagates through the optical system in a manner strongly influenced by diffraction effects as well as by the normal refractive effects of lens surfaces of the optical system. In addition to providing the magnified image of end face 64B which defines cross-sectional shape of the beam, i.e., the treatment-spot shape, the optical system must also project the beam waist, correspondingly magnified into treatment plane 26. The magnified beam waist WM will have essentially the same cross-sectional uniformity of intensity as the beam waist W at exit-face 64B of lightguide 64.

Any beam waist occupies a volume on the optical axis of the optical system. The beam-waist volume is usually defined by a nominal location, being that of the narrowest dimension of the waist, and a length defined by the distance between the nominal waist-location and a location at which the waist has a dimension equal the narrowest waist dimension multiplied by the square root of two, i.e., 1.414 WM. This is known as the "Rayleigh range". Within this range (±R), the intensity distribution characteristics of the beam across any axial location can be considered to be practically about the same. At exit-face 64B of lightguide the nominal waist-location of the emergent beam and the plane of the exit-face are coincident.

The propagation characteristics of the exit-face image and its emergent beam through an optical system are influenced by different factors as discussed above. Unless these different factors are considered, the image of the optical fiber exit-face and magnified projection of its emerging beam-waist can arrive at different axial locations in image space. This can result in that at no axial position in the image space of the lens would there be a location at which the laser beam would have a uniform intensity distribution and edge definition usefully approaching that immediately adjacent the optical fiber exit-face.

In formulating the above described optical systems, it was been determined that a uniformly-illuminated, well-defined treatment-spot can be projected in treatment plane 26 when the magnified image 64M of the endface of the light is in the treatment plane and the treatment plane is located within one Rayleigh range (within ±R) of the nominal location of a projection of the beam waist WM at the lightguide exit-face. The term "projection" is used here and in the appended claims to differentiate between what might be described as a "volume image" of the waist and a two-dimensional image as understood in refractive ray tracing methods. Those skilled in the art will recognize that in optical systems such as systems 40B–E, the projected beam waist will be scanned together with the lightguide exit-face image, in a plane parallel to treatment plane 26.

In summary an inventive handpiece for delivering electromagnetic radiation to tissue to be treated is described above. The handpiece includes an inventive arrangement for shaping the radiation to be delivered into a treatment-spot having an angular, i.e., polygonal, shape. The spot-shape is provided by passing the radiation through a lightguide having a cross section of the same shape before projecting the radiation via a plurality of lenses to form the spot. The shape is preferably selected such that a plurality of such shapes can completely cover an area of tissue to be treated essentially without overlap. The handpiece includes a scanning arrangement for scanning the treatment-spot over an area to be treated that is greater than the area of the treatment-spot. It should be noted that the inventive spot-shaping arrangement is also useful in a handpiece that does not include any scanning arrangement. Using such a handpiece, a large are of tissue can be treated by manually moving the handpiece over the area.

The handpiece, in certain above-described embodiments thereof, also includes an inventive spot scanning arrangement. The inventive scanning arrangement involves causing relative motion between the spot-shaping lightguide and one or more of the projecting lenses. The inventive scanning arrangement is also useful in a handpiece that is not required to deliver a polygonal treatment-spot. In such a handpiece, the polygonal lightguide may be replaced by a conventional circular-cross-section optical fiber which could be a fiber transporting the electromagnetic radiation from a source thereof, such as a laser, to the handpiece.

The handpiece of the present invention is described above in terms of a preferred and other embodiments. The invention is not limited, however, to the embodiments described and depicted. Rather the invention is limited only by the claims appended hereto.

What is claimed is:

1. A method of delivering electromagnetic radiation onto a tissue to be treated with the electromagnetic radiation, the method comprising the steps of:
   (a) providing a lightguide having a polygonal cross-section of a predetermined shape;
   (b) directing the radiation into said lightguide;
   (c) projecting an image of an exit-face of said lightguide onto the tissue to be treated such that the electromagnetic radiation is delivered onto said tissue in a treatment-spot having the polygonal shape of said lightguide cross section; and
   (d) scanning said projected image while maintaining said lightguide stationary relative to said tissue, so as to treat a continuous region of the tissue, said region having an area greater than the area of said treatment-spot.

2. The method of claim 1, wherein said polygonal shape is selected such that a plurality of said shapes can completely fill said area to be treated essentially without overlapping each other.

3. The method of claim 2, wherein said polygonal shape is one of a rectangle and a hexagon.

4. The method of claim 1, wherein said lightguide has a length sufficient that radiation directed therealong has a substantially uniform intensity distribution over said exit-face thereof.

5. The method of claim 4, wherein said lightguide length is less than about 50 millimeters.

6. The method of claim 4, wherein, during step (b), said radiation directed into said lightguide merges from said exit-face thereof as a beam having said substantially uniform energy distribution.

7. The method of claim 6, wherein said treatment-spot has a substantially uniform radiation intensity distribution therein.

8. The method of claim 7, wherein said uniformity of radiation intensity in said treatment region is less than about ±20% of a predetermined nominal value.

9. A method of delivering electromagnetic radiation onto a region of tissue to be treated with the electromagnetic radiation, the method comprising the steps of:
   (a) providing an optical system, said optical system including a lightguide having an exit-face, and having a polygonal cross-section of a predetermined shape, said lightguide having a length sufficient that radiation directed therealong has a substantially uniform intensity distribution over am exit-face thereof, said optical system further including a plurality of lenses arranged o an optical axis to project an image of said lightguide exit-face, said projected area having an area less than the area of said area of tissue to be treated;
   (b) directing the radiation into said lightguide such that a beam of said radiation emerges from said lightguide t said exit-face thereof, said beam having substantial uniform energy distribution at said exit face;
   (c) projecting said image of said lightguide exit-face and said beam of radiation emerging therefrom onto the tissue to be treated such that the radiation is delivered onto said tissue in a treatment-spot having the polygonal shape of said lightguide cross-section, a substantially uniform energy distribution therein, and an area less than the area of said area of tissue to be treated; and
   (d) during step (c) moving said treatment-spot over said region of tissue while maintaining said optical system stationary relative to said region of tissue, such that said region of tissue is entirely irradiated with an about uniform intensity distribution of said radiation.

10. The method of claim 9, wherein treatment-spot moving is accomplished by causing relative movement transverse to said optical axis between said exit-face of said lightguide one or more of said plurality of lenses.

11. The method of claim 9, wherein said treatment-spot moving is accomplished by a galvanometer mirror arrangement located between two of said plurality of lenses.

12. The method of claim 11, wherein said treatment-spot moving is accomplished with said optical system in a fixed location relative to said region of tissue.

13. The method of claim 11, wherein said treatment-spot moving is accomplished by moving said optical system relative to said region of tissue.

14. A method of delivering electromagnetic radiation onto a tissue to be treated with the electromagnetic radiation, the method comprising the steps of:
   (a) providing a lightguide having a polygonal cross-section of a predetermined shape;
   (b) directing the radiation through said lightguide such that a beam of said radiation emerges from said light guide;
   (c) projecting said be of radiation onto the tissue such that the radiation is delivered to the tissue in a treatment-spot having the shape of the lightguide cross-section; and
   (d) scanning said beam while maintaining said lightguide stationary relative to said tissue, so as to treat a continuous region of the tissue, said region having an area greater than the area of said treatment-spot.

15. A method of delivering electromagnetic radiation onto a region of tissue to be treated with the electromagnetic radiation, the method comprising the steps of:
   (a) providing a light de having a polygonal cross-section of a predetermined shape;

(b) directing the radiation through said lightguide such that a beam of said radiation emerges from said lightguide at an exit-face thereof, said emerging beam having a substantially uniform energy distribution at said lightguide exit-face;

(c) projecting said emerging beam of radiation the region of tissue such that the radiation is delivered to the tissue in a treatment-spot having the shape of the lightguide cross-section, and having an area less than area of the region of tissue, said projection is arranged such that said treatment-spot correspondingly has a substantially uniform intensity of irradiation there ; and (d) during step (c) continuously moving said treatment-spot while maintaining said lightguide stationary relative to said tissue, such that the region of tissue is about uniformly irradiated by the radiation delivered thereto.

16. The method of claim 15, wherein said predetermined shape is rectangular.

17. A method of delivering electromagnetic radiation onto a region of tissue to be treated with the electromagnetic radiation, the method comprising the steps of:

(a) providing a lightguide having a cross-section of a predetermined polygonal shape;

(b) directing the radiation through said lightguide such that a beam of said radiation emerges from said lightguide at an exit-face thereof, said emerging beam having a substantially uniform energy distribution at said lightguide exit-face;

(c) periodically projecting said emerging beam of radiation onto the region of tissue such that the radiation is delivered to the tissue in a sequence of treatment-spots each thereof having the shape of the lightguide cross-section and having an area less than area of the region of tissue, said projection being arranged such that each of said treatment-spots correspondingly has a substantially uniform intensity of irradiation therein;

(d) during step (c) delivering said sequence of spots in a pattern while maintaining said lightguide stationary relative to said tissue, such that the region of tissue is substantially uniformly irradiated by the delivered radiation.

* * * * *